US008802404B2

(12) United States Patent
Durant et al.

(10) Patent No.: US 8,802,404 B2
(45) Date of Patent: Aug. 12, 2014

(54) VINYL ACID MONOMER RECOVERY

(75) Inventors: Jennifer Durant, Lee, NH (US); Yvon Durant, Lee, NH (US); John Shaw, Hampton Falls, NH (US)

(73) Assignees: University of New Hampshire, Durham, NH (US); Itaconix Corporation, Stratham, NH (US)

( * ) Notice: Subject to any disclaimer, the term of this patent is extended or adjusted under 35 U.S.C. 154(b) by 244 days.

(21) Appl. No.: 13/081,187

(22) Filed: Apr. 6, 2011

(65) Prior Publication Data

US 2012/0258510 A1 Oct. 11, 2012

(51) Int. Cl.
*C12P 7/44* (2006.01)
*C12N 15/31* (2006.01)

(52) U.S. Cl.
USPC ........................................ 435/142; 435/252.1

(58) Field of Classification Search
None
See application file for complete search history.

(56) References Cited

U.S. PATENT DOCUMENTS

| 5,223,592 | A | 6/1993 | Hughes et al. |
|---|---|---|---|
| 5,336,744 | A | 8/1994 | Swift et al. |
| 5,457,040 | A | 10/1995 | Jarry et al. |
| 5,552,316 | A | 9/1996 | Savage |
| 7,910,676 | B2 | 3/2011 | Durant et al. |
| 7,910,677 | B2 | 3/2011 | Durant et al. |
| 7,915,365 | B2 | 3/2011 | Durant et al. |
| 8,227,560 | B2 | 7/2012 | Durant et al. |
| 8,642,298 | B2 | 2/2014 | Van Der Werf et al. |
| 2009/0269812 | A1 | 10/2009 | Sawai et al. |
| 2009/0286947 | A1 | 11/2009 | Durant et al. |
| 2010/0016153 | A1 | 1/2010 | Durant et al. |
| 2010/0022436 | A1 | 1/2010 | Durant et al. |

OTHER PUBLICATIONS

International Search Report and Written Opinion dated Jul. 13, 2012 issued in related International Patent Application No. PCT/US12/31510.

*Primary Examiner* — Anand Desai
(74) *Attorney, Agent, or Firm* — Grossman, Tucker, Perreault & Pfleger, PLLC

(57) ABSTRACT

The present disclosure relates to a method for recovering a vinyl acid monomer by providing an aqueous fermentation broth which undergoes microbial fermentation of a nutrient medium containing a carbon source including at least one microorganism to produce a vinyl acid monomer. The method provides a direct overall route to bio-based polymers of the vinyl acid monomer, and in particular, polymers of polyitaconic acid.

20 Claims, 3 Drawing Sheets

VINYL ACID MONOMER RECOVERY

FIELD OF THE INVENTION

The present invention relates to the recovery of polymers of vinyl type monomers that may contain pendant carboxylic acid groups which groups may ultimately be configured in metallic salt form. The monomers are recovered at concentrations and purity levels that may be particularly suitable for ensuing polymerization under selected conditions of partial neutralization to provide relatively high conversions and/or relatively high values of molecular weight and/or selected amounts of repeating unit tacticity.

BACKGROUND OF THE INVENTION

The polymerization of vinyl type monomers that contain pendant carboxylic acid functionality has always presented some unique challenges. For example, U.S. Pat. No. 5,223,592 reports that the critical aspect is to provide complete neutralization of an itaconic acid type monomer prior to conducting the polymerization reaction, where complete neutralization is identified as having two moles of base neutralizer for each mole of itaconic acid. U.S. Pat. No. 5,336,744 reports that polymers of itaconic acid are formed at high conversion by an aqueous polymerization process of partially neutralized monomer solution, water, polyvalent metal ion, and initiator.

Attention is also directed to: (1) U.S. Publication No. 2009/0286847 entitled
"Polycarboxylic Acid Polymers" which relates to methods and polymer based upon vinyl type monomers that contain pendant carboxylic acid groups and ester group functionality; (2) U.S. Publication No. 2010/0016153 which relates to absorbent materials and polymers used in absorbent materials based upon vinyl type monomers that contain pendant carboxylic acid groups and ester functionality; (3) U.S. Publications No. 2010/0022436 which relates to polymers based upon vinyl type monomers that contain pendant carboxylic acid groups and ester functionality that may be used in detergent formulations.

SUMMARY

The present disclosure relates to a method for recovering a vinyl acid monomer by providing an aqueous fermentation broth which undergoes microbial fermentation of a nutrient medium containing a carbon source including at least one microorganism to produce a vinyl acid monomer. This may then be followed by reactive extraction of the vinyl acid monomer from the aqueous fermentation broth into an organic phase by exposure to a hydrophobic Lewis base having a solubility in water of less than or equal to 1.0 g/L, wherein the vinyl acid monomer is present in a salt form in an organic phase. The extraction may also utilize a hydrophobic active modifier and hydrophobic diluent. The extraction may then be followed by exposing the vinyl acid salt in the organic phase to an aqueous phase containing a base and recovering the vinyl acid salt in an aqueous phase as a partially neutralized salt of the vinyl acid monomer.

In related embodiment, the present disclosure relates to method for recovering a vinyl acid monomer by providing an aqueous fermentation broth which undergoes microbial fermentation of a nutrient medium containing a carbon source including at least one microorganism to produce a vinyl acid monomer wherein the vinyl acid monomer has the following structure:

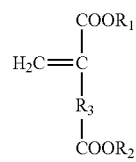

wherein $R_1$ and $R_2$ are selected from a hydrogen atom or an alkyl group or an aromatic group, or a cyclic alkyl group or a polyether, and combinations thereof and $R_3$ is selected from an alkyl group, aromatic functionality, heteroaromatic functionality, cyclic alkyl group, heterocylic group, or combinations thereof, wherein at least 50 mole % of $R_1$ and $R_2$ are a hydrogen atom to provide carboxylic acid functionality. This may then be followed by extracting 50% or more of the vinyl acid monomer from the aqueous fermentation broth into an organic phase by exposure to a hydrophobic Lewis base having a solubility in water of less than or equal to 1.0 g/L, wherein the vinyl acid monomer is present in a salt form in the organic phase. This may then be followed by exposing the vinyl acid salt in the organic phase to an aqueous phase containing a base and recovering the vinyl acid salt in an aqueous phase as a partially neutralized salt of the vinyl acid monomer.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
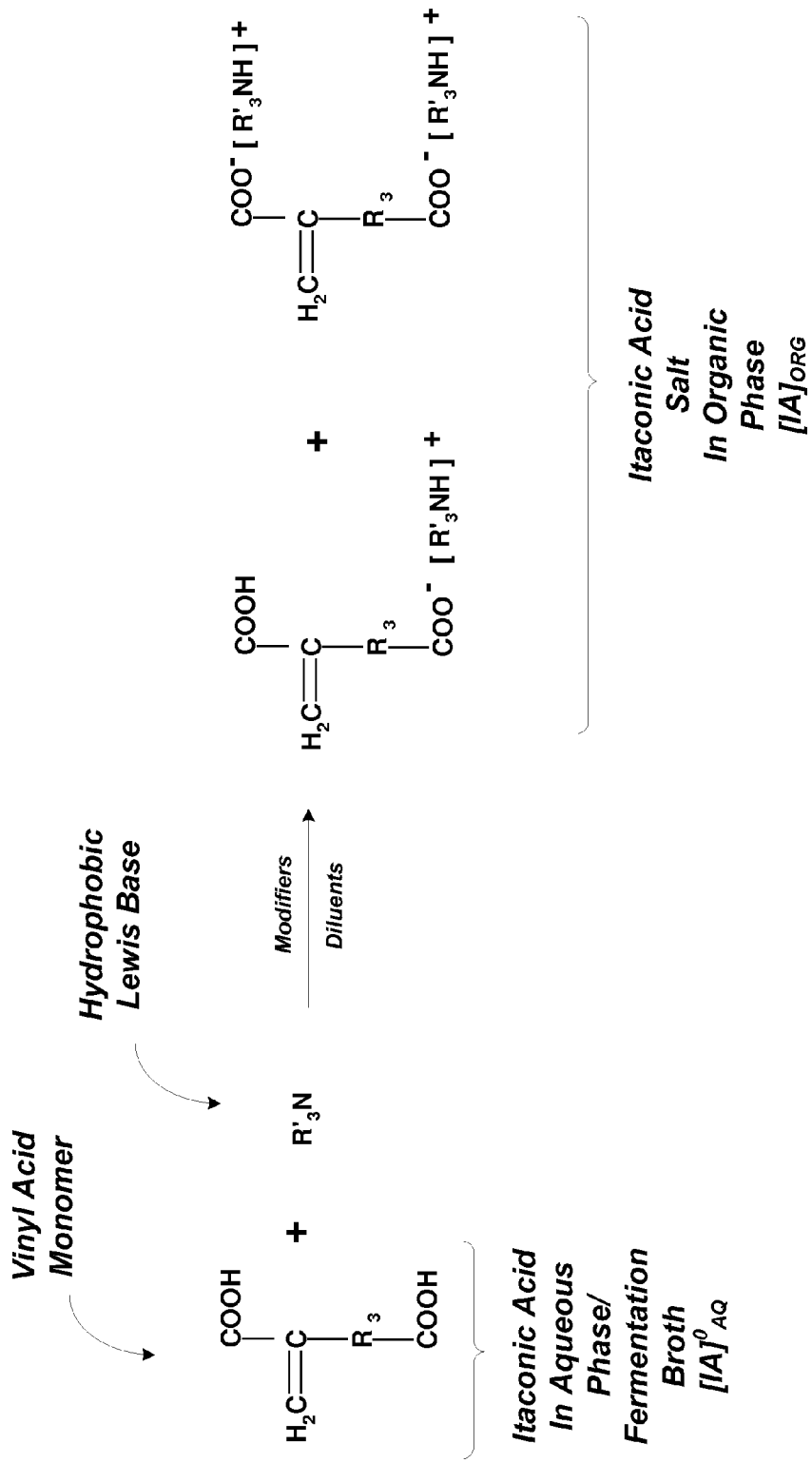
FIG. 1 illustrates the first step of reactive extraction of a vinyl acid monomer from an aqueous fermentation bath into the organic phase utilizing a hydrophobic Lewis base wherein the vinyl acid monomer (R=—CH$_2$—) is itaconic acid in the form of an acidic salt.

The present invention relates to the recovery of polymers of vinyl type monomers that may contain pendant carboxylic acid groups which groups may be in metallic salt form. The recovery methods herein may now provide a direct overall route to bio-based polymers from renewable resources which polymers may be utilized for applications such as: (1) detergents (industrial and household detergents); (2) water treatment (flocculants and anti-scaling agents); (3) absorbing polymers (fluid absorbent for such as diapers and water management for the agricultural industry); and (4) thickening/viscosity modifiers (ink binders, drilling and mud modification, dispersant in paper coatings, fiber sizing, sequestrant in mining operations and emulsifiers in cosmetics).

The vinyl type monomers that may be recovered herein may have the following structure:

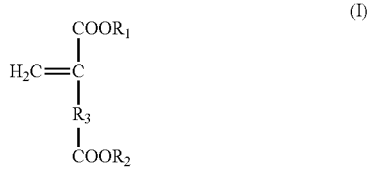

wherein $R_1$ and $R_2$ are selected from a hydrogen atom or an alkyl group (e.g. —($C_nH_{2n+1}$) where n has a value of 1-18), or an aromatic group, or a cyclic alkyl group or a polyether, and combinations thereof. In addition, $R_3$ may be selected from an alkyl group, aromatic functionality, heteroaromatic functionality, cyclic alkyl group, heterocylic group, or combinations thereof, wherein at least 50 mole % of $R_1$ and $R_2$ are a hydrogen atom to provide carboxylic acid functionality. In addition, in a particularly preferred embodiment, $R_1$ and $R_2$ are both hydrogen atoms, which therefore provides the monomer generally known as itaconic acid.

Vinyl type monomer recovery herein is now preferably sourced from a fermentation broth of a carbon source nutrient, such as a sugar, which may be understood as a mixture of microorganisms and nutrients which produce various fermentation products. More generally, the fermentation broth may include a mixture of microorganisms, nutrients (carbon and nitrogen source) and micronutrients, gases such as oxygen and other gases which may influence the metabolic process, and the fermentation products. In addition, the broth may include other chemical additives such as pH regulators and/or anti-foaming agents. The recovery procedure is now described with regards to the particular features of the methodology and composition as more fully detailed below.

Microorganisms

The microorganisms that are preferred within the fermentation broth include any microorganism that is capable of producing a fermentation product that includes the vinyl type monomer structures noted above, and in particular, itaconic acid. Preferably, the microorganisms include but are not limited to the genus *Aspergillus* and preferably may include *Aspergillus terreus, Aspergillus itaconicus* and *Aspergillus niger*. Others microorganisms that are contemplated herein include *Usilago zeae, Helicobasidium mompa, Candia* (yeast) and *Pseudozyma antarctica*.

In addition, preferably, a secondary metabolism may now be induced in the microorganisms to promote the formation of the preferred vinyl monomer of itaconic acid. This may be achieved by phosphate-limited growth in most cases but nitrogen-limited growth may also be employed (e.g. *P. antarctica*). In that context, it is noted that the cells generally require a source of carbon, nitrogen, phosphate and minerals to grow (generate mycelium). By depriving the cells of sufficient phosphate (i.e. phosphate-limited) in the production stage, one may now redirect metabolic energy from cell growth to the secondary metabolite production noted above (i.e. itaconic acid). Phosphate can be provided in the form of potassium phosphate at the concentration range of 0 to 0.2 g/L, preferably in the range of 0 to 0.1 g/L, with production of itaconic acid being particularly enhanced when the phosphate concentration is less than or equal to 0.01 g/L or in the range of 0.001 g/L to 0.01 g/L.

Nutrients

The carbon source nutrients that may be employed in the fermentation broth include mono- and disaccharides, such as glucose, sucrose, fructose, hydrolyzed starches and molasses as they exist in a form that may be assimilated by the microorganisms. Preferably, the nutrients may include D-glucose. The nutrients may also be selected from natural oils such as corn oil. One may also utilize ethanol, glycerol, inulin, D-mannose, cellobiose and D-xylose. Such nutrients may be present in the fermentation broth at an initial concentration range of 2% to 40%, preferably at a concentration range of 5% to 15%, and supplemented by semi-continuous addition during the fermentation in order to sustain a concentration range of 5 to 15%.

The fermentation broth also contains inorganic salts based upon Ca, Mg, Na, K, Fe, Ni, Co, Cu, Mn, and Zn, which salts may be those of a halogen (e.g. a chloride salt), a sulfate salt and/or phosphate salt. For example, the salts may preferably include one or more of $ZnSO_4$, $CuSO_4$, or $FeSO_4$. Such salts may be present in the fermentation broth at a concentration range of 0.0001 to 0.25 g/L preferably at a concentration range of 0.002 to 0.02 g/L, additional salt such as $MgSO_4$ and $CaCl_2$ may be present in the fermentation broth at a concentration range of 0.1 g/L to 10.0 g/L, preferably 0.1 g/L to 1.0 g/L for $MgSO_4$ and 1.0 g/L to 10.0 g/L for $CaCl_2$. A source of nitrogen may also be present in the fermentation broth, such as amino acids for natural source, urea, or ammonium nitrate ($NH_4NO_3$), in a concentration range of 0.001 to 20.0 g/L, preferably at the concentration range of 1.0 g/L to 4.0 g/L. One may also employ corn steep liquor as a source of minerals, either on its own, or in conjunction with additional salt as described therein.

Extraction

The reactive solvent extraction herein may be understood as an extraction method wherein the fermentation broth is exposed to a Lewis base (electron pair receptor) that is also hydrophobic (non-water soluble). For example, preferably, the Lewis base herein may comprise a tertiary amine ($R'_3N$) wherein the R' groups are selected from appropriate organic group functionality (e.g. alkyl, substituted alkyl, aromatic or substituted aromatic) to provide a requisite hydrophobic performance which may be understood as sufficient hydrophobicity to promote the recovery of the vinyl acid monomer from the aqueous phase broth into the organic phase as the initial part of the recovery procedure. Alkyl group herein is reference to aliphatic hydrocarbon type structure which may include alkane, alkene and/or alkyne type functionality and aromatic functionality may be understood to include benzene type structure. In addition, the Lewis base herein may preferably comprise a phosphate of the formula $(R'O)_3PO$ wherein the R' groups are again selected from appropriate organic group functionality (e.g. alkyl, substituted alkyl, aromatic or substituted aromatic) to provide the requisite hydrophobic performance. Accordingly, the Lewis base herein may be selected from those Lewis base compounds that provide a solubility in water of less than or equal to 1.0 g/L. More preferably, the solubility in water of the Lewis base may be less than or equal to 0.01 g/L and even more preferably, less than or equal to 0.001 g/L. Preferably, the tertiary amine herein specifically includes an alkyl type substituted tertiary amine such as tri-n-octyl amine.

The extraction herein is also preferably carried out in the presence of an active modifier, which may be understood has any organic compound that has a polar component (i.e. an atom or linkage that will provide the compound with polarity beyond that of a Van der Waals force) that also provides requisite hydrophobic performance. That is, the active modifier, similar to the Lewis base noted above, preferably has a solubility in water of less than or equal to 0.1 g/L. More preferably, the solubility in water of the active modifier may be less than or equal to 0.01 g/L and even more preferably, less than or equal to 0.001 g/L. The active modifier may therefore generally comprise an organic alcohol (ROH) where the number of carbon atoms in the R group is equal to or greater than eight. Accordingly, R may be an alkyl group of the type [(—CH$_2$)$_7$—CH$_3$] or an isomer of such configuration, and may also include cyclic and or aromatic functionality. It may therefore be appreciated that preferably, the active modifier herein may include octanol, nonanol and/or decanol.

Extraction here is also preferably carried out in the presence of an inert diluent, which may be understood as any organic hydrocarbon that again has the requisite hydrophobicity That is, the inert diluents is one that has a water solubility of less than or equal to 0.1 g/L. More preferably, the solubility in water of the Lewis base may be less than or equal to 0.01 g/L and even more preferably, less than or equal to 0.001 g/L. Preferably, the diluent is of alkane type functionality, and may include heptanes or kerosene and mixture of hydrocarbons. Preferably, the role of the diluents is to reduce the viscosity during the reactive extraction procedure.

From the above it may now therefore be appreciated that the extraction media preferably includes: (1) Lewis base; (2) active modifier and (3) inert diluents. The level of each of these components in the extraction media may be adjusted and be as follows: Lewis base at 1.0 to 40.0 vol. %; active modifier at 0.1 to 40.0 vol. percent and the remainder comprising the inert diluent. More preferably, the Lewis base may be present at a range of 20.0 to 35.0 vol. %, active modifier may be present at 10.0 to 35.0 vol. %, and the remainder once again comprising the inert diluent. As to be discussed herein, the selection of such ingredients is one that may ultimately provide a recovered bio-based vinyl acid monomer that has appropriate neutralization of the pendant carboxylic acid groups for effective polymerization.

Temperature

The extraction procedure herein is preferably temperature controlled. With regards to temperature control, extraction is preferably accomplished at temperatures in the range of 15.0° C. to 90° C. More preferably, extraction is carried out at temperatures in the range of 25.0° C. to 40° C.

Attention is now directed to FIG. 1, which illustrates the reactive solvent extraction as applied to the preferred recovery of an exemplary monomer, itaconic acid, utilizing a hydrophobic Lewis base (tertiary amine). As can be appreciated, by reactively extracting the itaconic acid from the aqueous fermentation broth (simultaneous conversion to a salt) in the presence of a hydrophobic Lewis base and in the presence of the active hydrophobic modifier (e.g. an alkyl chain alcohol) and hydrophobic diluents (e.g. organic hydrocarbon) noted herein, the itaconic acid undergoes a transfer from the aqueous phase into the organic phase, and is provided in the form of an organic salt which may be preferably monovalent and/or possibly divalent. Furthermore, the hydrophobic modifier (alkyl chain alcohol) is configured to be co-solvating and may assist in stabilizing the itaconic acid salt in the organic phase. The inert diluent may also operate to support the presence of the itaconic acid salt in the organic phase while also functioning to regulate the viscosity of the salt medium in the organic phase. The viscosity of the salt in the organic phase may at this point be in the range of 1 mPa·s to 100mPa·s preferably in the range of 2 mPa·s to 10 mPa·s.

Accordingly, what may be observed as significant at this point in the description of this methodology is that a vinyl type acid monomer from a bio-based aqueous phase fermentation media may be configured to undergo the indicated phase change in the overall recovery procedure disclosed herein.

The itaconic acid salt in the organic phase in FIG. 1 may then next be exposed to a basic aqueous solution containing an inorganic base, e.g., M$^+$[OH]$^-$ where M may be a metal or an appropriate cationic moiety, such as may be the case in sodium hydroxide, potassium hydroxide, ammonium hydroxide, barium hydroxide, calcium hydroxide, etc. This step may be understood as a stripping operation where the exemplary itaconic acid is removed from the organic phase and introduced in the aqueous phase in salt form. Preferably, one may utilize an inorganic base solution wherein the inorganic base is present at a concentration of 10-50 wt. %. Upon exposure to such metal hydroxides, the pH will preferably be adjusted in the range of 4.0-6.0. More preferably, the pH will have the value of 4.8 which value may vary +/−1.0. Even more preferably, the pH may have a value of 4.8 at +/−0.3 and in a most preferred embodiment the pH may have a value of 4.8 at +/−0.1. The stripping operation is preferably carried out at temperatures between 25.0° C. and 90.0° C., and more preferably, at temperatures between 50.0° C. and 90.0° C.

It should also be noted that the extraction and stripping operations may be preferably done sequentially and continuously to optimize the isolation of the salt of the vinyl acid for ensuing polymerization procedures. For example, with regards to the extraction step, the ratio of the aqueous broth feed volume to extraction solvent volume may be between 0.1 to 10, more preferably, 0.5 to 5.0. With regards to the stripping step, the ratio of the aqueous inorganic base phase to the organic phase containing the vinyl acid salt of the Lewis base is between 0.1 to 10, preferably 0.2 to 2.0, more preferably 0.25 to 1.0. All told, the level of vinyl acid salt recovery may be in the range of 50 to 500 g/L preferably 100 to 350 g/L. In addition, the recovered vinyl acid salt may be further purified using activated carbon.

Figure 2:
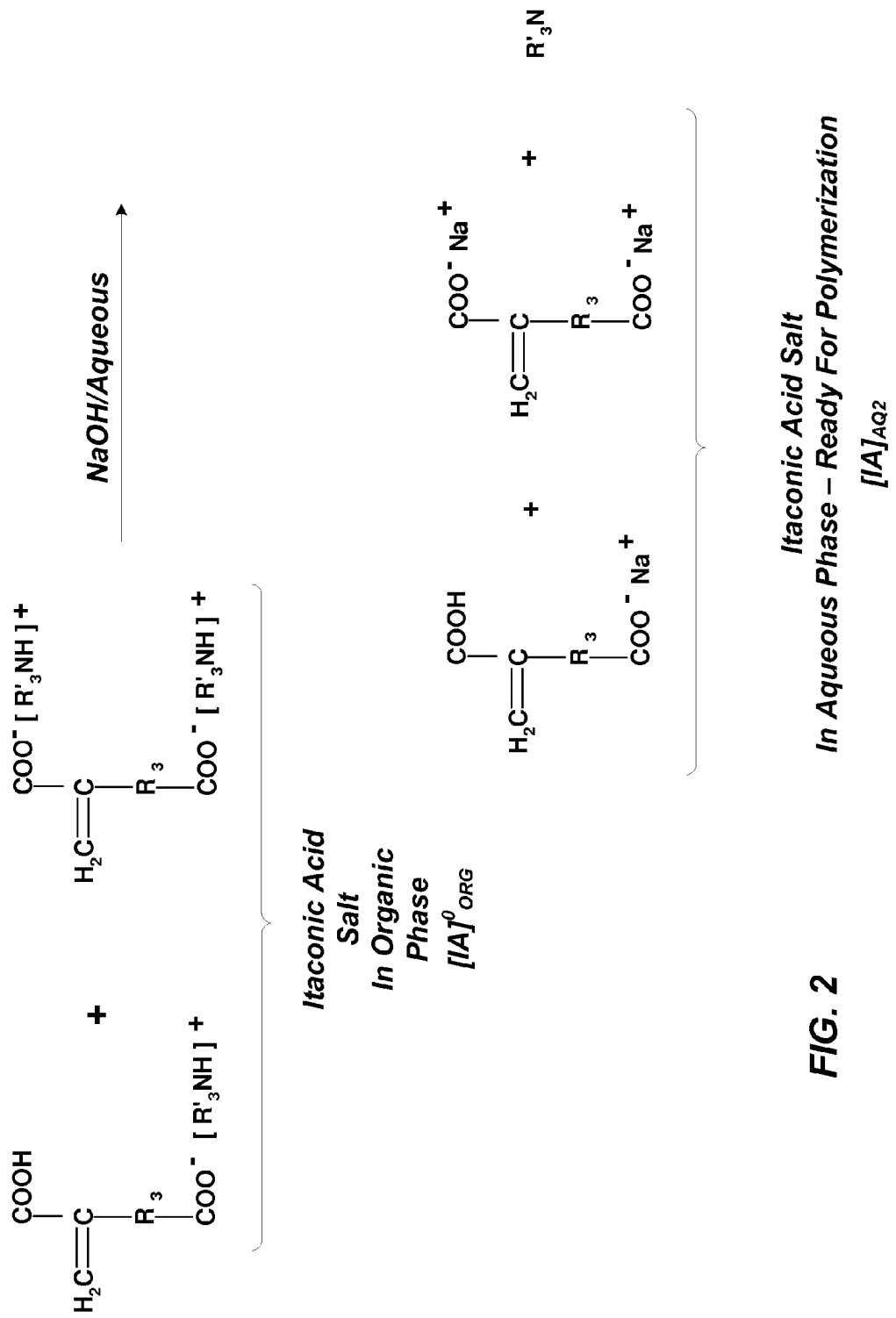
FIG. 2 illustrates the conversion of the itaconic acid salt in FIG. 1 (R=—CH$_2$—) into a partially neutralized salt in aqueous phase that is ready for ensuing polymerization.

FIG. 2 now illustrates the above referenced stripping of the Lewis base of the vinyl acid monomer via the use of sodium hydroxide solution. As can be seen, the itaconic acid salt is conveniently converted to the partially neutralized secondary salt in the aqueous phase with the generation of the tertiary amine compound. That being established, it is noted that the neutralization herein can be adjusted to provide less than a complete neutralization of the acidic groups present in the vinyl monomers.

Figure 3:
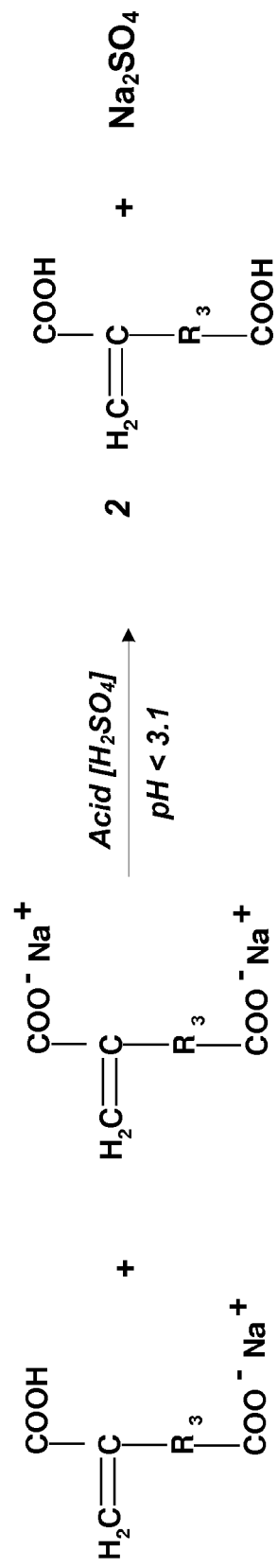
FIG. 3 illustrates the optional exposure of the partially neutralized vinyl acid in the aqueous phase shown in FIG. 2 to relatively strong acid to yield the vinyl acid in protonated form.

However, before discussing the ability to control neutralization to provide less than a complete neutralization of the acidic groups in the recovered vinyl acid monomers, it should be noted that optionally, one may expose the partially neutralized vinyl acid monomer to relatively strong acid (e.g. an inorganic acid such as HCl or H$_2$SO$_4$) to provide a pH of less than or equal to 3.1, such as in the range of 0.5 to 3.1, to yield the vinyl acid in protonated form dispersed in a solution of inorganic salt. See FIG. 3. Accordingly, the pH may be 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 or 3.1. The vinyl acid in protonated form will typically be crystalline which will then facilitate its recovery from the aqueous phase.

Returning then to the significance of providing less than complete neutralization of the vinyl acid monomer, this is particularly significant as it now builds upon the disclosure in U.S. Publication No. 2009/0286847 entitled "Polycarboxylic Acid Polymers" which relates to methods and polymer based upon vinyl type monomers that contain pendant carboxylic acid groups and ester group functionality. More specifically, the recovery of the vinyl acid monomer from the fermentation broth herein now provides an entirely bio-based route to polymers containing pendant acid group functionality.

Accordingly the amount of neutralization and isolation in the aqueous phase (FIG. 2) may ultimately be adjusted to provide a less than complete neutralization of the acidic groups present on the vinyl monomers. For example, in the case of the representative monomer of itaconic acid, it may be understood that complete neutralization will require two moles of neutralizer (NaOH) for each mole of itaconic acid. That is, two moles of sodium hydroxide would provide complete neutralization of one mole of itaconic acid, and any amount of sodium hydroxide less than two moles would provide the desired result of partial neutralization. Those of skill in the art would recognize that when a divalent based is employed to neutralize itaconic acid, the amount of divalent base selected to completely neutralize itaconic acid would be 1.0 mole of divalent base for each mole of itaconic acid, and to partially neutralize, less than one mole of divalent base may be applied to partially neutralize the itaconic acid monomer.

It has been found that the ultimate level of neutralization herein from the recovery of the fermentation broth and isolation of the vinyl type monomers in the aqueous phase (FIG. 2) may be preferentially maintained at about 25.0 mole % to 85.0 mole %, including all values therein, in 1.0 mole % increments. For example, for 1.0 moles of itaconic acid, one may preferably neutralize 0.25 moles of the acid groups present to 0.85 moles of the acid groups present. More preferably, the level of neutralization of the itaconic acid salt in the aqueous phase and ready for polymerization may be maintained at a level of 40.0 mole % to 60.0 mole %, and in a most preferred embodiment, the level of neutralization of the acid monomer selected may be in the range of 45.0 mole % to 55.0 mole %.

The temperature of the stripping operation in FIG. 2 and at which partial neutralization may be achieved may also be preferably adjusted such that neutralization is accomplished at temperatures of 50.0° C. to 150° C., including all values therein, in 1.0° C. increments. For example, it is preferable that the neutralization temperature for the sequence illustrated in FIG. 2 is adjusted to be 50° C. to 110° C., and in a most preferred configuration, the neutralization temperature is adjusted to be in the range of 65° C. to 100° C.

The time for neutralization and recovery of the vinyl acid monomer in the aqueous phase for polymerization (FIG. 2) has also emerged as another variable to regulate and may also be selected herein to occur for a selected and relatively limited period of time prior to any ensuing polymerization. For example, one may partially neutralize according to the requirements noted above and allow for such partial neutralization to remain at the previously specified neutralization temperatures for a period of time up to and including 6.0 hours, including all time periods between 0.1 hours to 6.0 hours, in 0.1 hourly increments. More preferably, the neutralization time period at the previously specified temperature may be selected such that it does not exceed a time period of 2.0 hours. Finally, the neutralization time period at the previously specified temperature may be preferably selected such that it does not exceed a time period of 1.0 hours.

In addition, it may be appreciated that one may accomplish the neutralization with sodium hydroxide in FIG. 2 by, e.g., operating for no more than an accumulated time period of 6.0 hours at a temperature of 50° C. to 150° C., by cooling outside such temperature and time period, to otherwise limit isomerization of the recovered monomers, as discussed more fully below. For example, one may partially neutralize as noted above for a period of 0.5 hours at a temperature of 50° C. to 150° C., then cool to about 25° C. This may then be followed by heating and neutralizing for another 0.5 hours at a temperature of 50° C. to 150° C. This then would provide a preferred time and temperature of neutralization, prior to polymerization, of 1.0 hours at a temperature of 50° C. to 150° C.

With respect to the above disclosure regarding the control of neutralization of the acidic vinyl monomers, and in particular, the representative monomer of itaconic acid, it is noted that the use of partial neutralization in the process of FIG. 2, at the indicated neutralization temperatures and/or at the indicated neutralization times, may again provide for the ability to minimize the isomerization of the vinyl acid monomer (e.g. itaconic acid) to chain terminating structures (i.e. compounds that impede the conversion itaconic acid to poly (itaconic acid). For example, the level of chain terminator, which may be formed from the acidic vinyl monomers may now be controlled to be present at or below the level of 20.0 mole percent, for each mole of acidic vinyl monomer that is initially present. More preferably, the level of chain terminator sourced from the acidic vinyl monomer may be controlled, through the neutralization procedures noted herein, to be present at levels of at or below 10.0 mole percent for each mole of acidic vinyl monomer, and in the most preferred embodiment, such level of chain terminator is controlled to be present at or below 5.0 mole percent. For example, the level of chain terminator may preferentially be adjusted to be in the range of 0.1 mole percent to 5.0 mole percent.

One representative example of the formation of chain terminator from a vinyl acidic monomer again points to the representative use of itaconic acid. More specifically, it is contemplated that itaconic acid may rearrange to provide citraconic acid or mesaconic acid, according to the following general equation, which citraconic or mesaconic acid, as a tri-substituted vinyl monomer, is believed to retard polymerization conversion and/or molecular weight.

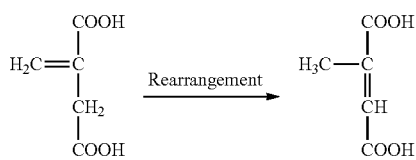

Polymerization

Subsequent to neutralization according to FIG. 2, according to the use of the partial neutralization noted herein at the indicated windows of, e.g., time and temperature, polymerization may be initiated. Initially, the vinyl monomers noted herein containing acidic functionality may be combined in a solvent to provide a solids content of 50 wt. % to 90 wt. %, including all values therein in 1.0 wt. % increments. The solids content may more preferably be in the range of 60 wt. % to 80 wt. % or 65 wt. % to 75 wt. %. Solids content may be understood as the wt. % of monomer in the solvent that is employed.

One may then employ radical initiation, utilizing free radical initiators such as peroxides and azo compounds, such as azobisisobutyronitrile (AIBN). One may also preferably utilize water-soluble radical initiators wherein the initiators are prepared in solution by dissolving the selected initiator in deionized water or a combination of water miscible polar solvents. Water soluble initiators may include persulfate salts, such as ammonium persulfate, sodium persulfate and potassium persulfate, including mixtures thereof. Also useful as a water soluble initiator are hydrogen peroxide ($H_2O_2$), tertiobutyl hydroperoxide, and water soluble azo initiators.

The initiators may be present at the concentration of 0.05 wt. % to 15.0 wt. % of monomer present, and all values therein, at 0.05 wt. % increments. More preferably, the initiators may be present at a level of 0.10 wt. % to 6.0 wt. % of monomer present, or at a level of 0.20 wt. % to 4.0 wt. % of the monomer present. In addition, the initiators may be selected such that they have an effective temperature for a 10.0 hour half-life $(T10)_{1/2}$, or time to decrease to half of their initial concentration, of less than or equal to 100° C. In other words, preferentially, the initiators are selected such that less than half of the initiator remains present after 10 hours, at temperatures above 100° C. In this manner, it can be assured that sufficient free radicals are generated during the polymerization.

The initiator may be sequentially introduced into the polymerization solution (monomer and solvent) by introducing the herein disclosed amount of initiator over the first 75% of the time assigned for polymerization. For example, for a 3 hour polymerization period, one may introduce the initiator such that the first 50% of all initiator to be added is introduced at the start of the polymerization period, and the remaining 50% is added over the 2.25 hours. Furthermore, one may elect to add all of the desired amount of initiator at the start of the selected polymerization period. However, it may be preferred to utilize sequential addition, as this may support continuous polymerization processes.

The solution of monomer and solvent, subsequent to the neutralization procedures noted herein, may then be heated to a temperature of 50° C. to 150° C., including all values therein in 1.0° C. increments. More preferably, the polymerization temperature may be set to 70° C. to 115° C. or 80° C. to 110° C. In addition, the time for polymerization of the monomers may be from 0.1 hours to 48 hours, including all values therein, in 0.1 hour increments. More preferably, the time for polymerization may be set to a time period of 0.2 hours to 12.0 hours or 0.3 hours to 3.0 hours.

Polymer MW And Tacticity

The polymers produced herein have been found to have weight average molecular weights (Mw) at or above 20,000 g/mole, and number average molecular weights (Mn) at or above 5,000 g/mole. More specifically, the values of Mw obtained herein may be in the range of 20,000 to 1,000,000 g/mole including all values therein, in increments of 1000. For example, Mw values that may be obtained herein may be in the range of 20,000 to 350,000 g/mole. Similarly, Mn values may be in the range of 5,000 to 25,000 g/mole including all values therein in increments of 1000.

It is also contemplated herein that one may, e.g., combine and react the monomers under the neutralization conditions noted herein (e.g. partially neutralizing the acid functionality at a level of 25.0 mole % to 85.0 mole %) for each mole of carboxylic acid functionality present, wherein said partial neutralization takes place over a time period not to exceed 6.0 hours at a temperature of 50° C. to 150° C.), such that the above MW values are obtained. Then, one may optionally introduce crosslinking, which may be achieved by the introduction of a monomer that provides crosslinking (e.g. a monomer containing 3 or more vinyl groups). In such manner, the polymers produced herein may become part of a crosslinked network while maintaining their indicated functionality characteristics for the substituents $R_1$, $R_2$ and $R_3$, noted herein.

The polymers prepared herein may also have a desired level of tacticity with respect to the analysis of triad structure by NMR techniques. For example, the polymers herein may specifically be formed with the presence of syndiotactic triads, at a level of greater than 58.0%. For example, the level of syndiotactic triads as determined by NMR techniques, such as $^{13}C$ NMR, may be formed at the level of greater than 58.0% to 75.0%, including all values therein, in 1.0% increments.

Below are now presented various working examples to illustrate the present disclosure. From a general equipment perspective, the recovery that has now been described herein may be accomplished with different processing equipment, which may include batch separatory funnel sedimentation with optional centrifugation and continuous dual hollow fiber modules. In that later case, the dual hollow fiber (HF) system may be used to extract and strip the vinyl acid monomer simultaneously.

The dual HF modules are a set of baffled, microporous membrane contactors that achieve liquid/liquid mass transfer of the vinyl acid monomer without dispersion of one phase in another. This may avoid the possibility of emulsion formation found in conventional methods. Furthermore a density difference is not necessary. Each module contains hundreds of bound fibers configured such that there is a shell and lumen side flow.

In the first module the aqueous vinyl acid monomer (broth) is passed to the organic phase. In the second module the IA is pulled out of the organic phase into the alkali solution. Both processes may happen simultaneously such that the organic solvent carrier is continuously regenerated. A slight (3-4 psi) overpressure is maintained in the aqueous loops to contain the organic phase in the lumen, which would otherwise pass through the hydrophobic membrane. The device may be run in a reverse configuration as well, whereby the organic phase is passed through the shell sides. However, running solvent through the lumen requires a relatively smaller volume of (expensive) solvent. A single module may also be run such that solvent is embedded in the pore structure and aqueous phases are then passed on either side of the pores. In this configuration, very little solvent is necessary but long term stability of the organic barrier can be an issue and as such, it is preferably to operate with 2 modules.

EXAMPLE I

A 60 g/L itaconic acid solution at pH 3.0 was diluted serially. The aqueous solutions were mixed with a ternary solvent system comprised of 20% (V/V) Trioctyl amine (T), 20% (v/v) decanol, and kerosene as diluent. The volume ratio was 1:1. The mixtures were agitated for 2 hours followed by 14 hrs settling to allow phase disengagement. The recovered organic phase was placed in contact with an equal volume of 0.5 M NaOH. After 1 hour of agitation, the resulting solutions were centrifuged at 10,000 g and the aqueous portion removed. The resulting aqueous phase had a pH of 4.9 was analyzed by HPLC and itaconic acid concentration was 35 g/L.

EXAMPLE II

A solutions of 60 g/L itaconic acid at pH 3.0 was mixed at 1:1 volume ratios with 0.46M TOA, 20% (v/v) octanol, and kerosene so as to produce the TOA/IA ratios shown in the table included below. The mixtures were agitated for 2 hours followed by 14 hrs settling to allow phase disengagement. The aqueous portion was set aside and the recovered organic phase for each sample was placed in contact with equal volume of 0.5 M NaOH. The resulting aqueous phase was analyzed by HPLC for itaconic acid concentration to calculate extraction $([IA]_{ORG}/[IA]^0_{AQ1})$ and stripping $([IA]_{AQ2}/[IA]^0_{ORG})$ efficiencies. It may be noted that the extraction efficiency of the present disclosure (see FIG. 1) and stripping efficiency (see FIG. 2) will be at a level of at least 50.0%, and may be configured to be at a level of 50.0%-99.0%.

|                       | Molar Ratio |    |    |    |    |
|-----------------------|-----|-----|-----|-----|-----|
|                       | 0   | 0.5 | 1.0 | 1.5 | 2   |
| Extraction Efficiency | 5   | 57  | 83  | 93  | 96  |
| Stripping Efficiency  | 95  | 95  | 97  | 89  | 87  |

EXAMPLE III

Fresh fermentation broth (*Aspergillus terreus*, pH 2.1) containing 22.9 g/L IA was aliquoted and spiked with additional IA to generate 3 different concentrations of 40, 50 and 60 g/L that would otherwise had identical residual broth composition in salts, proteins and residual sugars. The broths were mixed with a ternary solvent system comprised of 20% (v/v) TOA, 20% (v/v) octanol, and kerosene as diluent. The volume ratio was 1:1. The mixtures were agitated for 2 hours followed by 14 hrs settling to allow phase disengagement. The recovered organic phase for each sample was placed in contact with equal volume of 0.5 M NaOH. After 1 hour of agitation, the resulting solutions were centrifuged at 10,000 g and the aqueous portion removed. The resulting aqueous phase was analyzed by HPLC for itaconic acid concentration and pH.

|                       | Initial IA (g/L) |     |     |
|-----------------------|-----|-----|-----|
|                       | 60  | 50  | 40  |
| Partition Coefficient | 1.5 | 1.3 | 1.2 |
| Resulting pH          | 5.0 | 5.5 | 6.1 |

EXAMPLE IV

Two hollow fiber modules (4×13, LiquiCell X40, Membrana) were assembled such that 3 continuous loops could be operated: (1) itaconic acid solution (2) solvent system (3) stripping solution. An itaconic acid solution (2 L, 60.0 g/L acid, pH 2.2) was circulated through the shell side of module 1. The ternary organic solvent system (20% TOA, 20% octanol, heptane) was circulated through the lumen of both modules. Lastly, aqueous sodium hydroxide (0.46 M) was circulated shell side of module 2. The volume ratios were 1:1:1. The three loops were run at 0.5 L/min. The simultaneous extraction and stripping were monitored for IA concentration and pH. In 7 hours 63% was recovered (5.4 g/L-hr) and the pH dropped to 4.7. The run was allowed to proceed overnight (25 hours total) resulting in an overall 78% recovery in the form of monosodium itaconate from the fermentation broth.

EXAMPLE V

Two hollow fiber modules (4×13, LiquiCell X40, Membrana) were assembled such that 3 continuous loops could be operated: (1) broth (2) solvent system (3) stripping solution. Fermentation broth (2 L, 61.1 g/L acid, pH 2.1) was circulated through the shell side of module 1. The ternary organic solvent system (0.46 M Alamine 336, 20% decanol, kerosene) was circulated through the lumen of both modules. Lastly, aqueous sodium hydroxide (0.46 M) was circulated shell side of module 2. The volume ratios were 1:1:1. The aqueous and organic phases were run at 0.5 and 1 L/min, respectively. The simultaneous extraction and stripping were monitored for IA concentration and pH. In 7 hours 90% was recovered (7.8 g/L-hr) and the pH dropped to 5.0. The run was allowed to proceed overnight (23 hours total) resulting in an overall 97% recovery in the form of monosodium itaconate from the fermentation broth.

EXAMPLE VI

After fermentation (*A. terreus*), the brown broth was clarified via filtration (0.22 um). The IA content was measured at 43 g/L by HPLC and the pH at 2.0. Broth was contacted with equal volume of extraction system (carrier/modifier/diluent=Alamine 336/decanol/kerosene) in a separatory funnel. The loaded organic phase was then stripped with sodium hydroxide to yield an aqueous IA solution at pH 5.2. The pH was adjusted to pH 4.7+/−0.15 with HCl. The product was concentrated as is in a rotary evaporator. The moisture content was measured and found to be 13.9%. The sample was diluted to give 73% w/w and heated to 80° C. to give a liquid solution. 2% w/w sodium persulfate was then added, mixed, and the solution allowed to polymerize for 2 hours at 80° C. Gel Permeation Chromatography (GPC) analysis showed that a 52% monomer to polymer conversion was achieved.

EXAMPLE VII

Example VI was repeated but with a portion of the same clarified broth treated first with activated carbon. Darco S-51 (Norit) was used at 80 g/L for 2 hours, with mechanical agitation at 150 rpm, at room temperature. The resulting filtered broth was completely clear. Concentration yielded a solid with a 16.37% moisture content. The solution was adjusted to 73% w/w and polymerized as described in example VI. GPC analysis showed that a 92% monomer to polymer conversion was achieved.

EXAMPLE VIII

After recovery with hollow fiber modules similar to that described in Example IV, the resulting monosodium itaconate solution at pH 4.7 was concentrated to a moisture content of 8.9%. After heading to 85° C., the solution concentration was adjusted to 75% w/w and 2% w/w sodium persulfate was then mixed in thoroughly and heated for 2 hours. The conversion measured by GPC was 96%.

EXAMPLE IX

Monosodium itaconate recovered from broth with hollow fiber modules, as described in Example V, was concentrated by rotary evaporation. The resulting solution was adjusted to pH 4.8 and a concentration of 72% w/w and polymerized at 80° C. with 2 wt % sodium persulfate. GPC analysis showed 65% conversion.

EXAMPLE X

Itaconic acid broth obtained from an industrial molasses fermentation was recovered using the hollow fiber system described in example V. The resulting product stream had a pH of 4.9 and was concentrated to a concentration of 71 wt %. Polymerization was carried at 80° C. for 2.3 hours resulting in a 63% conversion (measured by GPC).

EXAMPLE XI

A 99 g/L aqueous solution of Ba(OH)2-8H20 was prepared and kept at 60° C. Itaconic acid (60 g/L) was added to organic solvent (0.46M alamine 336, 20% decanol, kerosene). A 1:1 volume ratio of the barium solution and loaded organic solutions were contacted at room temperature and kept under constant shaking at 60° C. for 30 minutes. After phase disengagement aided by centrifugation (3,000 g for 10 minutes), the resulting aqueous barium solution contained an equivalent of 42.6 g/L IA in the form of monobarium itaconate, giving a stripping efficiency of 71%.

EXAMPLE XII 2600 grams of itaconic acid where dissolved in 1150 grams of water with 1600 grams of sodium hydroxide (50% w/w), at 60° C. to yield a clear solution of monosodium itaconate. Under mechanical stifling, 572 ml of sulfuric acid (93% w/w) where added at the rate of 10 ml/min, while the temperature was maintained at 60° C. The resulting slurry contained 2220 grams of crystalline itaconic acid, dispersed in a solution of sodium sulfate at 338 g/L, saturated in itaconic acid. Upon filtration, rinsing of the crystal with 30° C. water, and drying in a vacuum oven, high purity crystalline itaconic acid was recovered.

What is claimed is:

1. A method for recovering itaconic acid monomer by:
   (a) providing an aqueous fermentation broth which undergoes microbial fermentation of a nutrient medium containing a carbon source including at least one microorganism to produce itaconic acid;
   (b) extracting the itaconic acid from said aqueous fermentation broth into an organic phase by exposure to a hydrophobic Lewis base having a solubility in water of less than or equal to 1.0 g/L, wherein the itaconic acid monomer is present in a salt form in said organic phase;
   (c) exposing said itaconic acid salt in said organic phase to an aqueous phase containing a base and recovering said itaconic acid salt in an aqueous phase as a partially neutralized salt of said itaconic acid monomer.

2. The method of claim 1 wherein said hydrophobic Lewis base comprises a tertiary amine ($R_3N$) wherein the R groups are selected from one of an alkyl group, substituted alkyl group, aromatic group, or substituted aromatic group.

3. The method of claim 1 wherein said hydrophobic Lewis base comprises a phosphate having the formula $(RO)_3PO$ wherein the R groups are selected from one of an alkyl group, substituted alkyl group, aromatic group, or substituted aromatic group.

4. The method of claim 1 wherein the extraction is carried out in the additional presence of a polar organic compound that has a solubility in water of less than or equal to 0.1 g/L.

5. The method of claim 1 including the additional step of exposing said partially neutralized salt of said vinyl acid monomer to acid and reducing the pH to at or below 3.1 and converting said partially neutralized salt of said vinyl acid monomer to vinyl acid monomer.

6. The method of claim 4 wherein the additional polar organic compound comprises an organic alcohol having eight or more carbon atoms.

7. The method of claim 1 wherein said extraction is carried out in the additional presence of an organic diluents which reduces the viscosity of the extraction media and which diluent has a water solubility of less than or equal to 0.1 g/L.

8. The method of claim 1 wherein said Lewis base is present at a level of 1.0 to 40.0 vol. %.

9. The method of claim 1 wherein extraction is carried out at a temperature of 15.0° C. to 90° C.

10. The method of claim 1 wherein in step (c), said base comprises $M^+[OH]^-$ wherein M is selected from K, Na, $NH_4$.

11. The method of claim 1 wherein in step (c) said base comprises $M^+([OH]^-)_2$ where M is selected from Ca or Ba.

12. The method of claim 1 wherein said partially neutralized salt of said vinyl acid monomer recovered in step (c) has a partial neutralization of 25.0 mole % to 85.0 mole %.

13. The method of claim 1 wherein 50.0% or more of said vinyl acid monomer from said aqueous fermentation broth is converted into said salt form of said vinyl acid monomer in said organic phase.

14. The method of claim 1 wherein 50.0% or more of said vinyl acid monomer in said organic phase is converted to said partially neutralized salt of said vinyl acid monomer in said aqueous phase.

15. The method of claim 1 wherein said itaconic acid producing microorganism comprises a microorganism of the genus *Aspergillus*.

16. The method of claim 15 wherein said microorganism comprises *Aspergillus terreus, Asperfillus itaconicus* or *Aspergillus niger*.

17. The method of claim 1 wherein said itaconic acid producing microorganism comprises *Utsilago aeae, Helicobasidium mompa, Candia* or *Pseudozyma antartica*.

18. The method of claim 1 wherein said nutrient medium containing a carbon source comprises a mono- or disaccharides, corn oil, ethanol, glycerol, inulin, D-mannose, cellobiose, or D-xylose.

19. The method of claim 1 wherein said nutrient medium comprises an inorganic salt of Ca, Mg, Na, K, Fe, Ni, Co, Cu, Mn, or Zn.

20. The method of claim 1 wherein said nutrient medium comprises a source of nitrogen comprising an amino acid, urea, or ammonium nitrate.

* * * * *